US008198067B2

(12) United States Patent
Kyle

(10) Patent No.: US 8,198,067 B2
(45) Date of Patent: Jun. 12, 2012

(54) DELIVERY OF DISEASE CONTROL IN AQUACULTURE AND AGRICULTURE USING MICROBES CONTAINING BIOACTIVE PROTEINS

(75) Inventor: David J. Kyle, Catonsville, MD (US)

(73) Assignee: Advanced Bionutrtion Corporation, Columbia, MD (US)

( * ) Notice: Subject to any disclaimer, the term of this patent is extended or adjusted under 35 U.S.C. 154(b) by 424 days.

(21) Appl. No.: 11/449,829

(22) Filed: Jun. 9, 2006

(65) Prior Publication Data
US 2006/0263820 A1 Nov. 23, 2006

Related U.S. Application Data

(60) Division of application No. 10/654,985, filed on Sep. 5, 2003, which is a continuation-in-part of application No. PCT/US02/08651, filed on Mar. 22, 2002.

(60) Provisional application No. 60/277,947, filed on Mar. 23, 2001.

(51) Int. Cl.
C12N 1/14 (2006.01)
A61K 38/00 (2006.01)
A23K 1/17 (2006.01)

(52) U.S. Cl. .................. 435/257.2; 435/257.1; 514/2.2; 514/2.3; 514/2.4; 424/439; 424/442

(58) Field of Classification Search .................. None
See application file for complete search history.

(56) References Cited

U.S. PATENT DOCUMENTS

| 3,983,008 | A | * | 9/1976 | Shinozaki et al. | 435/190 |
| RE32,333 | E | * | 1/1987 | Hamill et al. | 530/321 |
| 5,047,250 | A | * | 9/1991 | Prieels et al. | 426/2 |
| 5,270,175 | A | | 12/1993 | Moll | |
| 5,281,596 | A | | 1/1994 | Kitao et al. | |
| 5,661,017 | A | | 8/1997 | Dunahay et al. | |
| 5,681,557 | A | | 10/1997 | Grabstein et al. | |
| 5,830,463 | A | * | 11/1998 | Duke et al. | 424/93.51 |
| 5,968,809 | A | * | 10/1999 | Knutzon et al. | 435/254.2 |
| 5,977,437 | A | | 11/1999 | Villand et al. | |
| 6,027,900 | A | | 2/2000 | Allnutt et al. | |
| 6,100,388 | A | | 8/2000 | Casas et al. | |
| 6,156,517 | A | | 12/2000 | Mayfield | |
| 6,294,653 | B1 | | 9/2001 | Mayfield | |
| 6,399,074 | B1 | | 6/2002 | Roland | |
| 6,462,027 | B2 | | 10/2002 | Poet et al. | |
| 2002/0090376 | A1 | | 7/2002 | Kaniga et al. | |
| 2002/0102692 | A1 | | 8/2002 | Lei et al. | |
| 2003/0072772 | A1 | | 4/2003 | Vakharia | |

FOREIGN PATENT DOCUMENTS

| CA | 2442004 | | 5/2002 |
| EP | 0971034 | | 1/2000 |
| JP | 73032672 | B * | 10/1973 |
| JP | 3170465 | | 11/1990 |
| JP | 403030691 | A * | 2/1991 |
| WO | WO 90/07578 | | 7/1990 |
| WO | WO 95/35389 | | 12/1995 |
| WO | WO 97/14806 | | 4/1997 |
| WO | WO 98/42748 | | 1/1998 |
| WO | 00/04919 | | 2/2000 |
| WO | WO 01/96871 | | 12/2001 |
| WO | WO 01/98335 | | 12/2001 |
| WO | WO 02/15721 | | 2/2002 |
| WO | WO 02 076391 | | 10/2002 |

OTHER PUBLICATIONS

MacKenzie et al., "Isolation and use of a homologous histone H4 promoter and a ribosomal DNA region in a transformation vector for the oil-producing fungus Mortierella alpina," Applied and Environmental Microbiology; vol. 66 No. 11, pp. 4655-4661 (Nov. 2000).*
Tuse et al., "Single-cell protein: current status and future prospects," Critical Reviews in Food Science and Nutrition, vol. 19 No. 4, pp. 273-325 (1984).*
Abstract Translation, JP 73032672 B, Oct. 1973.*
Abstract Translation, JP 403030691A, Feb. 1991.*
Arakawa T, Yu J, Chong DK, Hough J, Engen PC, Langridge WH (1998) A plant-based cholera toxin B subunit-insulin fusion protein protects against the development of autoimmune diabetes. Nat Biotechnol., vol. 16, pp. 934-938.
Arakawa T, Yu J, Langridge WH (1999) Food Plant-Delivered Cholera Toxin B Subunit for Vaccination and Immunotolerization. Adv Exp Med Biol., vol. 464, pp. 161-178.
Arntzen CJ (1998) Pharmaceutical foodstuffs—oral immunization with transgenic plants. Nat Med vol. 4, pp. 502-503.
Burgess J, Tsubaki K, Matsunaga T (1993) Expression of Yellow Tail (Seriola Quinqueradiata) Fish Growth Hormone cDNA in the Marine Photosynthetic Bacterium Rhodobacter SP NKPB 0021, Biotechnol Lett., vol. 15, pp. 111-114.
Kim, DH et al. (2002) Stable Integration and Functional Expression of Flounder Growth Hormone Gene in Transformed Microalga, Chlorella ellipsoidea. Marine Biotechnol (NY), vol. 4, pp. 63-73.
Cregg JM, Cereghino JL, Shi J, Higgins DR (2000) Recombinant Protein Expression in Pichia pastoris. Mol Biotechnol., vol. 16, pp. 23-52.
Leong JC et al. (1997) Fish Vaccine Antigens Produced or Delivered by Recombinant DNA Technologies. Dev Biol Stand., vol. 90, pp. 267-277.
Maassen CB et al. (2000) Strain-dependent induction of cytokine profiles in the gut by orally administered *Lactobacillus strains*. Vaccine, vol. 18, pp. 2613-2623.
Mayfield S et al., (2001) Expression and assembly of a fully active antibody in algae. Proc. Natl. Acad. Sci., vol. 100, pp. 438-442.

(Continued)

Primary Examiner — Zachariah Lucas
(74) Attorney, Agent, or Firm — Marianne Fuierer; Moore & Van Allen, PLLC

(57) ABSTRACT

A microbial biomass, made from algae, bacteria, fungi, yeast, or combinations thereof, provides a feed for animals raised either in agriculture or aquaculture. A feed additive, and a therapeutic composition can also be made from a microbial biomass of algae, bacteria, fungi, yeast, or combinations thereof. The feed, feed additive, and therapeutic composition can comprise one or more proteins, peptides, antibodies, antibody fragments, or a combination thereof, wherein said proteins, peptides, antibodies, antibody fragments, or a combination thereof are non-native to the microbes of the biomass. The biomass can have therapeutic, bioactive, nutritional, and/or immunogenic properties.

4 Claims, 2 Drawing Sheets

OTHER PUBLICATIONS

Richter L, Mason HS, Amtzen CJ (1996) Transgenic Plants Created for Oral Immunization Against Diarrheal Diseases, J Travel Med., vol. 3, pp. 52-56.

Seto A et al. (1992) Production of Eicosapentaenoic Acid by a Marine Microalgae and Its Commercial Utilization for Aquaculture, Ind. App. Single Cell Oils, chap. 12, pp. 219-234.

Tacket CO, Mason HS, Losonsky G, Clements JD, Levine MM, Arntzen CJ (1998) Immunogenicity in humans of a recombinant bacterial antigen delivered in a transgenic potato. Nat Med., vol. 4, pp. 607-609.

* cited by examiner

DELIVERY OF DISEASE CONTROL IN AQUACULTURE AND AGRICULTURE USING MICROBES CONTAINING BIOACTIVE PROTEINS

CROSS-REFERENCE TO RELATED APPLICATIONS

This application is a division of application Ser. No. 10/654,985, filed Sep. 5, 2003; which is a continuation-in-part of pending application PCT/US2002/086551, filed Mar. 22, 2002; which claims the benefit of U.S. Provisional Application No. 60/277,947, filed Mar. 23, 2001; all of which are incorporated herein by reference.

BACKGROUND OF THE INVENTION

1. Field of the Invention

This invention is directed to animal feeds used in aquaculture or in agriculture, with microbial cells as components. These microbial cells contain exogenous peptides, proteins, and/or antibodies, which can convey resistance or immunity to pathogens (such as viral or bacterial), or otherwise improve the health and performance of the species that consume them. The microbial cells can be algae, bacteria, fungi, or yeast. The exogenous peptides, proteins, and/or antibodies can be expressed inside the microbial cells by direct genetic modification of the microbe or by infecting the microbe with a virus that has been altered to express the protein of interest. The invention is also directed to animal feed supplements and therapeutics with microbial cells as components.

2. Related Art

Plant products have been produced using specific genetic modification to express proteins and/or antibodies of therapeutic value. The group at the Boyce Thompson Institute at Cornell has cloned a viral coat protein into bananas capable delivering an oral vaccine when ingested by humans, but this concept has not been extended to microbes.

There are several plant biotech companies, such as Meristem, Large Scale Biology, and Prodigene, which are now expressing certain human therapeutic proteins, including antibodies, in plants. Large Scale Biology is expressing proteins in tobacco plants using a tobacco mosaic virus as a vector to produce the protein of interest. The protein is then isolated and purified from the plant material and used for human therapeutic purposes. In this way, the plant genome itself is actually not modified, but rather the genome of the infecting virus carries the gene of interest.

Recombinant microbes, including bacteria, yeast, and other fungi, have been used to produce human therapeutic proteins. However, such recombinant microbes have not been used in agriculture or agriculture, wherein the cultivated animal ingests the whole organism. Rather, to date, the recombinant organism has been used as a factory from which the therapeutic protein is isolated and purified prior to use.

Certain plant products have been produced that contain proteins and/or antibodies of therapeutic value. They have been produced by infecting the plant with a virus that expresses the protein of interest. Large Scale Biology has a series of patents protecting this technology, but its purpose is to produce purified proteins for pharmaceutical purposes, which requires an extensive purification procedure following harvesting of the plant material. These patents do not involve the use of the crude plant material as a source of both nutrition and disease control, except under the unusual condition that the pharmaceutical product is expressed in the fruit of the plant.

Certain recombinant proteins have been produced in insect cells using an insect virus expression system (baculovirus). These proteins are also produced in intact insect larvae following infection with modified baculoviruses. In both cases, the insect cells or larvae are used as factories to produce the protein of interest, and the recombinant protein is then purified for pharmaceutical purposes. Insect cells or larvae infected with baculovirus are particularly useful in the expression of certain human therapeutic proteins because the post-translational modifications of the therapeutic proteins are similar to the post-translational modifications imparted upon expression in human cells.

A baculovirus expression system is an efficient method for expressing proteins in insect cell culture. Baculovirus is in the family Baculoviridae, a diverse group of large double stranded DNA viruses that infect arthropods, including insects, arachnids, and crustaceans. Baculoviruses are species-specific and do not infect vertebrates, nor can they propagate in mammalian cells in culture.

The Sindbis arbovirus can be used to deliver high levels of gene expression in vivo in non-host arthropod species without causing cytopathic effects in infected cells or impairing the development of the organism. A replication competent Sindbis virus containing the coding region of green fluorescent protein (GFP) induced productive infections when injected into insect larvae and pupae (Lewis, et al., 1999). Thus, virus-mediated ectopic gene expression has been accomplished in arthropods, a phylum that includes the classes Crustacea and Insecta.

Antibiotic doping is used routinely in the aquaculture setting. Typically, the pure or semipure antibiotics are added directly to the water column. However, crude fermentation broths, or crude preparations including cells, have not been used for any kind of therapeutic delivery system.

Production of amino acids, such as lysine, typically involves a genetically modified microorganism, which overproduces the amino acid of interest and excretes it into the fermentation medium. The wastestream from such a fermentation would include biomass containing the amino acid, and this wastestream product could be used as a crude delivery form of the small molecule nutritive amino acid.

Microalgae (single celled algae or phytoplankton) represent the largest, but most poorly understood, kingdom of microorganisms on the earth. As plants are to terrestrial animals, microalgae represent the natural nutritional base and primary source of all the phytonutrients in the aquatic food chain. As the primary producers in the aquatic food chain, microalgae are the source of many phytonutrients, including docosahexaenoic acid (DHA) and arachidonic acid (ARA). Microalgae also represent a vast genetic resource, comprising in excess of 80,000 different species.

Yeast, filamentous fungi, and bacteria are also in the direct food chain of fish, crustaceans, and mollusks. However, only a very few of these microbes, perhaps less than 10 species, have been exploited for aquaculture feeds. These few species have been used primarily for historical reasons and ease of cultivation. They have not been chosen on the basis of any scientific evidence of superiority as nutritional or therapeutic supplements.

The marine environment is filled with bacteria and viruses that can attack fish and shellfish, thereby devastating aquaculture farms very quickly. Bacteria and viruses can also attack single celled microalgae, so these organisms have evolved biochemical mechanisms to defend themselves from such attacks. Such mechanisms may involve the secretion of probiotic compounds that inhibit bacterial growth or viral attachment.

SUMMARY OF THE INVENTION

The present invention provides a microbial biomass for use as a feed, feed additive, and/or therapeutic, and the use of such feed, feed additive, and/or therapeutic to deliver a therapeutic dose of a bioactive peptide or protein. The invention also provides a method for feeding the feed, feed additive, and/or therapeutic to animals cultivated in agriculture and aquaculture.

This invention provides an aquacultural or an agricultural feed containing microbial biomass comprising one or more peptides, proteins, antibodies, antibody fragments, or a combination thereof, where the proteins and antibodies are non-native to the microbes of the biomass. Preferably, the microbes are selected from yeast or other fungi, bacteria, algae, or combinations thereof. The microbes can be engineered to recombinantly express the proteins or antibodies recombinantly, or the microbes can be infected with viruses or plasmids, which express the recombinant proteins or antibodies, e.g., without altering the genome of the host organism.

This invention similarly provides feed additives for animals and therapeutic compositions for human and non-human animals. The biomass can be extracted or purified to produce the therapeutic compounds.

This invention also provides a method of delivering therapeutic proteins to an animal comprising administering a feed comprising one or more microbe expressing a non-native therapeutic protein to the animal. This method can be used to deliver therapeutic proteins to a non-human animal subjected to intensive agricultural practices, or to fish or shellfish in aquaculture. The therapeutic microbes can be algae, bacteria, yeast, or filamentous fungi. The therapeutic protein can be a recombinant protein expressed by the microbe, e.g., the microbe can be infected with a recombinant virus, which expresses a recombinant therapeutic or biactive protein. The method encompasses delivering therapeutic proteins that inhibit growth or replication of *Vibrio* species in vitro, and proteins or peptides that inhibit Taura Syndrome Virus (TSV) or White Spot Syndrome Virus (WSSV) infection in shrimp. It also encompasses recombinantly expressed antibodies, and fragments thereof.

Figure 1:
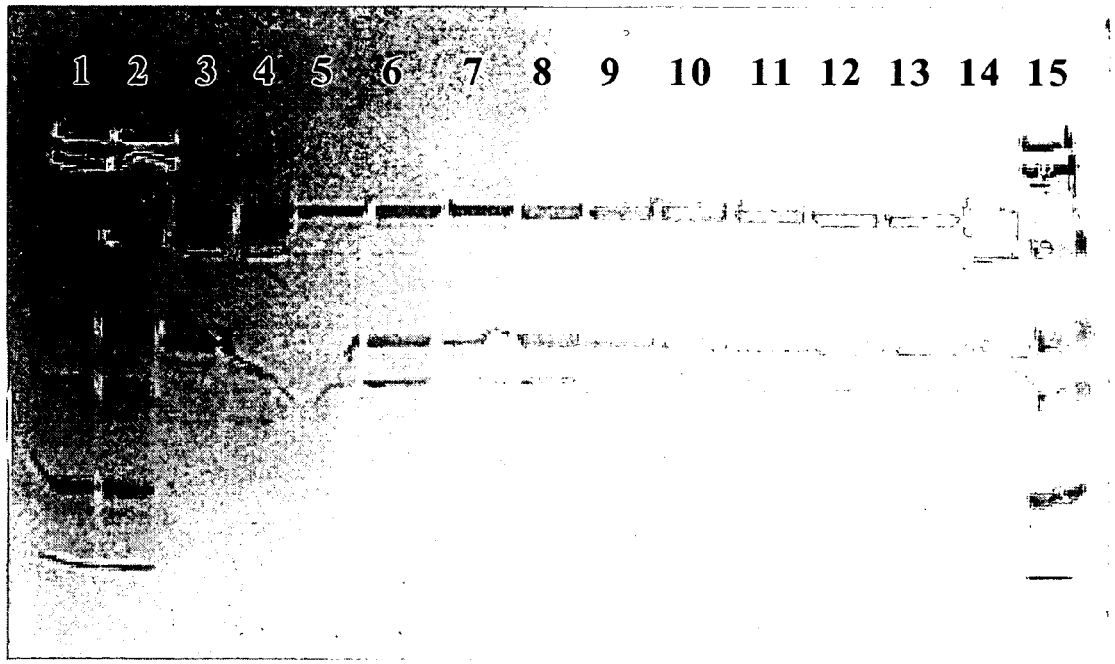
FIG. 1. Western blot of two *Saccharomyces cerevisiae* clones (A0244 and A0245) containing Infectious Pancreatic Necrosis Virus (IPNV) sequence encoding segment A (containing genes for VP2, VP4, and VP3). Lanes 1, 2, and 15 show BioRad low molecular weight standards. Lanes 3 and 4 show IPNV virus West Buxton strain proteins that are immunoreactive with a polyclonal antibody to IPNV. Lanes 5, 7, 9, 11, and 13 show clone A0244 proteins; and lanes 6, 8, 10, 12, and 14 show clone A0245 proteins that are immunoreactive with the polyclonal antibody to IPNV. The clones in lanes 5 and 6 were harvested at 120 hours post inoculation, the clones in lanes 7 and 8 at 96 hours, the clones in lanes 9 and 10 at 90 hours, the clones in lanes 11 and 12 at 72 hours, and the clones in lanes 13 and 14 at 64 hours.

FIG. 2. Expression of White Spot Virus (WSV) genes in *Escherichia coli* (BL21). His-tagged fusion proteins were detected with alkaline phosphatase with NBT/BCIP color development. Lane 1 is a negative control (pET28 clone, no insert), Lane 2 illustrates VP35, Lane 3 illustrates VP28, Lane 4 illustrates VP26, Lane 5 illustrates VP24, Lane 6 illustrates VP19, and Lane 7 contains molecular weight markers.

DETAILED DESCRIPTION OF THE INVENTION

Definitions

A "feed" is a preparation providing nutritional value to any animal, including, but not limited to, terrestrial animals, e.g., humans, cattle, horses, pigs, sheep, goats, and poultry; and aquatic animals, e.g., fish, shrimp, lobsters, crawfish, mollusks, sponges, and jellyfish.

A "feed additive" is any substance added to feed, regardless of nutritional or therapeutic value.

A "therapeutic" is a substance that can heal, or provide a remedial, palliative, or preventive effect on a pathologic process. Therapeutics can be used to treat medical diseases, conditions, or syndromes.

"Microalgae" include both prokaryotic and eukaryotic algae that are classed in many different species. Prokaryotic algae are typically referred to as cyanobacteria or bluegreen algae. Eukaryotic microalgae come from many different genera, some of which overlap with the macroalgae, but can be generally differentiated by their size and lack of defined organs. Microalgae can have specialized cell types. Examples of different groups containing microalgae include, but are not limited to, the chlorophyta, rhodophyta, phaeophyta, dinophyta, euglenophyta, cyanophyta, prochlorophyta, and cryptophyta.

An "antibiotic" is a substance that can inhibit or stop the growth of microorganisms, or that can kill microorganisms.

"Bactericidal" refers to the ability to kill bacteria. "Bacteriostatic" refers to the ability to inhibit or stop the growth of bacteria.

An "immunogenic epitope" is a discrete site of an antigenic molecule against which an antibody will be produced, to which the T-cell receptor responds, or to which an antibody can bind, and which is capable of inducing an immune response.

"Passive immunity" is immunity conveyed by molecules, e.g., antibodies, immunogens, other proteins, or sensitized lymphocytes, that deliver protection from antigens, and which is obtained from a source outside the organism's own immune system. Passive immunity can be acquired by an oral route, e.g. from an organism, antibody, or other molecule that enters the gastrointestinal system and provides immunity, e.g., by preventing infestation across the gastrointestinal mucosa, or by stimulating the gastrointestinal immune system, e.g., IgA antibodies, or gut-associated lymphoid tissue (GALT). Passive immunity can be also acquired by the transfer of antibodies from one animal to another, e.g., the passive immunity an offspring acquires from its mother.

"Aquaculture" is the cultivation of aquatic organisms under controlled conditions. An "aquatic organism" is an organism grown in water, either fresh- or saltwater. Aquatic organisms, include, but are not limited to, fish, e.g., bass, striped bass, tilapia, catfish, sea bream, rainbow trout, zebrafish, red drum, and carp; crustaceans, e.g., penaeid shrimp, brine shrimp, freshwater shrimp, and *Artemia*; and rotifers.

"Probiotic" refers to an organism or organisms important for the promotion of the growth of another organism. Probiotic effects, e.g., therapeutic or protective effects, can be delivered by probiotic organisms. Probiotic organisms include algae, bacteria, and fungi, such as yeast. Herein the term probiotic activity includes the production and/or secretion of a substance that defends the organism producing or secreting the substance from bacteria or viruses that is sometimes referred to as a prebiotic activity. For example, probiotics can inhibit bacterial and viral growth and attachment.

A "patient" is any living animal, including, but not limited to, a human who has, is susceptible to, or is suspected of having or being susceptible to, a pathologic condition, disease, or disorder, or who otherwise would be a subject of investigation relevant to a pathologic condition, disease, or disorder. Accordingly, a patient, can be an animal that has been bred or engineered as a model for any pathologic condition, disease, or disorder. Similarly, a patient can be an animal (such as a farm animal, a dairy animal, a ranch animal, an animal that lives under water, an animal cultivated on land or in water for food or other commercial use, an experimental animal, or a pet animal) including a human, who is serving as a healthy control for investigations into pathologic conditions, diseases, or disorders.

EMBODIMENTS OF THE INVENTION

Several algal species exhibit antibiotic activity. This activity can be due to certain bioactive constituents in the membranes or cell walls, the protein or the carbohydrate of the positively testing species that inhibit bacterial growth (prebiotics or herein probiotics). Any standard screening technique used to identify antibiotic agents can be used to screen for algae having antibiotic activity, including incubating filter disks soaked in culture broth from the candidate algae on a lawn of the target pathogenic microbe (e.g., *Vibrio* species). This invention contemplates the use of these "friendly algae" in a probiotic fashion to control the growth of certain pathogenic microorganisms in a pond. This invention is further directed to the use of recombinant microbes or virus-infected microbes to deliver a bioactive protein of choice. The recombinant microbes or virus-infected microbes can be tested for antibiotic activity by standard antibiotic screening assays to confirm their activity.

Historically, only bacteria have been used in a probiotic fashion to alter a pond's ecology in order to eliminate or reduce the number of pathogenic bacteria. A problem with the bacterial probiotic approach is that the existing microbial ecology represents a massive buffer that is difficult to modulate with the introduction of relatively small numbers of alternative bacteria, and the results to date have been unimpressive. Furthermore, even if the newly introduced bacteria do bloom, any large increase in bacterial levels in a pond can lower oxygen levels and cause harm to the other inhabitants, such as fish or shrimp.

Microalgae have not been considered before as probiotics. Previous experience in the screening of extensive algal culture collections has indicated that a number of algal species exhibit antibacterial or bacteriostatic capabilities. Some of these activities may include anti-*Vibrio* activity. Such species are candidates for a high value enrichment feed that delivers both nutritional and antibiotic capabilities. This invention provides an approach to disease control that provides a solution to an impending ecological disaster that will result from the present uncontrolled practice of dumping toxic chemicals and antibiotics into the water systems to control these bacterial; fungal, or viral pathogens.

Viral or bacteria infections can dramatically limit farm productivity in terrestrial environments. The marine environment is also filled with bacteria and viruses that can attack fish and/or shellfish. Infection by bacteria or viruses can devastate intensive marine-based farms very quickly. One of the major disease control problems in shrimp aquaculture today is infection by certain viruses (e.g. White Spot, Taura, etc.). Conventional strategies, e.g., antibiotics, are not effective in this situation, and shrimp cannot be vaccinated by methods analogous to those used for fish. Shrimp, like all crustaceans, have only a rudimentary immune system, so they are particularly susceptible to devastation by viral attacks.

This invention provides a solution to this problem with a biological control method using a microbial biomass, e.g., microalgae as a vector to deliver anti-White Spot antibodies directly to shrimp. Such "designer feeds" can be a normal part of the diet, and can deliver a therapeutic dose of antibody directly to the shrimp's gastrointestinal system. This provides passive immunity; the exogenous antibody remains outside the host organism and prevents infestation through the gut wall. The invention envisions the use of transgenic algae, yeast, fungi and/or bacteria to deliver the antibody to the virus. Such probiotics, as envisioned in the invention, do not have to replicate in the target organism for the desired effect to occur. Alternatively, the microbe itself may be infected with a virus that is engineered to produce the antibody of interest. Alternatively, the microbial source may deliver a portion of the virus (e.g. a coat protein or coat proteins) or fragment thereof, in order to immunize the shrimp, other shellfish, finfish, or other aquatic or terrestrial animals.

Antibodies, or antibody fragments, to desired targets, such as White Spot Syndrome Virus or Taura Syndrome Virus can be prepared by routine immunization techniques, e.g., and selection of monoclonal antibody producing hybridomas, or by screening viral or bacterial expression libraries of immunoglobulin genes and gene fragments. See. "Current Protocols in Immunology," Coligan, et al., eds, Wiley Interscience, 1991, and periodic supplements. Nucleic acid sequences encoding the binding sites of the selected antibodies can be cloned using standard methods (see "Current Protocols in Molecular Biology," Ausubel, et al., eds., Wiley-Interscience, 1987, and periodic supplements), and antibodies can be expressed from recombinant microbes (including algae, see, e.g., U.S. Pat. No. 6,027,900) or cloned into viruses that infect the desired microbes.

There are a number of well known bactericidal and bacteriostatic peptides that inhibit microbial growth. These include, but are not limited to, cecropins, penaeidins, bactenecins, callinectins, myticins, tachyplesins, clavanins, misgurins, pleurocidins, parasins, histones, acidic proteins, and lysozymes. These peptides can be made in a plant material such as tobacco, soybean, corn, sunflower, cotton, safflower, canola, or any other agronomic species using recombinant methods well known to those in the art, and thus provided as a feed component to convey resistance or tolerance to infestation. Suitable plant material also includes macroalgae (Kelps), which are grown worldwide as a commodity feed crop in aquaculture. Macroalgae are the foodstuffs of many aquaculture species, and this invention contemplates recombinant production of therapeutic proteins in the natural or farm diet of juvenile fish (e.g., half-grown catfish), as well as fish larvae. Thus, within the contemplation of this invention are macroalgae, or insects, or other host organisms that make up part of the food chain for the feeding of larvae, juveniles, and adults in aquaculture, as well as the same life sequence in the terrestrial animal feeds (e.g. pigs, chickens, and cows).

Post-harvest processing of some sort may be used to prepare the material for use as feeds. This invention contemplates conventional (known) processes for converting insect or plant material into feeds. Such conventional process includes homogenization followed by extrusion into pellets of various sizes, depending on the application (e.g., larval, juvenile, or adult). Other modes of preparation include spray drying, fluid bed drying, or even providing the material as a liquid suspension.

The invention provides a feed, feed additive, or therapeutic composition for an animal, which includes an algal biomass or any parts thereof, comprising one or more proteins, peptides, antibodies, antibody fragments, or combination thereof, which are non-native to the biomass, and which can be chosen from eukaryotic algae or prokaryotic algae sources.

The algal biomass can comprise heterotrophic and/or photosynthetic microalgae. The algae can be chosen from *Synechocystis*, and/or *Chlorella* strains. The algae can be probiotic.

The invention also provides proteins, peptides, antibodies, antibody fragments, or a combination(s) thereof which are expressed recombinantly, e.g., by a recombinant virus.

The invention further provides embodiments in which the proteins, peptides, antibodies, antibody fragments, or combination thereof inhibit the growth or replication of a pathogen, e.g., *Vibrio*, Taura Syndrome Virus, White Spot Syndrome Virus, and Infectious Pancreatic Necrosis Virus.

The invention further provides that the algal biomass, or an extract thereof, possesses antibiotic activity. The proteins, peptides, antibodies, antibody fragments, or a combination(s) thereof can be bactericidal and/or bacteriostatic. The protein, peptide, antibody, antibody fragment, or combination thereof can be, but is not necessarily, chosen from cecropins, penaeidins, bactenecins, callinectins, myticins, tachyplesins, clavanins, misgurins, pleurocidins, parasins, histones, acidic proteins, and lysozymes.

The invention provides that the protein, peptide, antibody, antibody fragment, or a combination(s) thereof comprises an immunogenic epitope.

The invention provides a method of feeding an animal comprising administering to the animal a feed, feed additive, or therapeutic composition that includes a microbial biomass, such as an algal, fungal, e.g., yeast, or bacterial biomass, or any parts thereof, as well as one or more proteins, peptides, antibodies, antibody fragments, or combination thereof, which are non-native to the algal, fungal, e.g., yeast, or bacterial biomass. The algal biomass can be chosen from eukaryotic algae or prokaryotic algae sources.

The invention also provides that the proteins, peptides, antibodies, antibody fragments, or combination thereof can confer passive immunity upon an animal. The animal can be raised in aquaculture, and can be a fish, e.g., a salmon, or a crustacean, e.g. a shrimp. Alternatively, the animal can be raised in agriculture, and can be cattle, porcine, or fowl. The animal can also be a human.

The invention additionally provides the embodiments, as described above in relation to algae, for yeast or other fungi, and bacteria. The yeast can comprise, e.g., a *Saccharomyces* strain. The fungi can comprise e.g., a *Mortierella* species. The bacteria can comprise e.g. a *Lactobacillus, Bacillus,* or *Bifidobacterium* species.

Certain embodiments of the invention will now be described in more detail through the following examples. The examples are intended solely to aid in more fully describing selected embodiments of the invention and should not be considered to limit the scope of the invention in any way.

EXAMPLES

Example 1

Selection of Useful Microbial Sources for Feeds that Provide Disease Control

Microalgal biomass samples, aqueous extracts, organic extracts, and extracts from the growth medium after cultivation of the algae were concentrated and spotted on filter paper discs. Using sterile techniques, these discs were then placed on agar plates overlaid with a lawn of selected test organisms including, but not limited to, gram-negative bacteria, gram-positive bacteria, antibiotic resistant bacteria, yeast, or other fungi. After incubation for an appropriate length of time to allow growth of the lawn of test organism, the plates were observed for zones of clearing (non-growth) around the filter paper discs. Large zones of clearing indicate potent antibiotic activity; small zones of clearing indicate less potent antibiotic activity.

Example 2

Incorporation of an Antibody Into an Algal Feed

A particular viral or bacterial pathogen is chosen and used to prepare monoclonal antibodies using procedures well known to those in this field (Harlow and Lane, eds., 1988. *Antibodies: A Laboratory Manual*, Cold Spring Harbor Laboratory Press). Gene(s) coding for this antibody or an appropriate antibody fragment ($F_{ab}$ or $F_v$) are isolated and amplified in the appropriate vector. The gene is spliced into a transformation vector suitable for a eukaryotic alga (e.g. *Chlorella*) or a prokaryotic alga (e.g. *Synechocystis*), or a yeast (e.g. *Saccharomyces*) or a fungus (e.g. *Mortierella*). The transformation vector is chosen so that the antibody will be over-expressed in the microbial cell biomass. This biomass is then used as a feed additive in such a way as to provide the antibody directly to the animal, thus providing passive immunity.

Example 3

Expression of a Bactericidal Protein in a Microbial Feed

A bactericidal protein is chosen for the particular application. For example, proteins of the penaeidin class may be chosen for pathogenic control in shrimp. Penaeidins are members of a family of antimicrobial peptides isolated from crustaceans (e.g., Penaeid shrimp). Antimicrobial peptides can also come from insects and chelicerates, and can include, but are not limited to, cecropins, peneaidins, bactenecins, callinectins, myticins, tachyplesins, clavanins, misgunins, pleurocidins, parasins, histones, acidic proteins, and lysozymes. The gene for the chosen protein or peptide is either isolated from the original source, an amplification source, or made synthetically. The gene is then incorporated into a transformation vector suitable for a eukaryotic alga (e.g. *Chlorella*) or a prokaryotic alga (e.g. *Synechocystis*), or a yeast (e.g. *Saccharomyces*) or a fungus (e.g. *Mortierella*). The transformation vector is chosen so that the protein will be over-expressed in the microbial cell biomass. This biomass is then used as a feed additive in such a way as to provide the bactericidal protein directly to the animal, thus providing resistance to that particular pathogen.

Example 4

Vaccination Using Feeds

An antigen characteristic of a particular pathogen is chosen as is indicated by the animal and circumstances. For example, a viral coat protein(s) or component thereof, or a protein from an infectious bacterium, or a component thereof, is chosen. The gene coding for the protein(s) is isolated and incorporated into a vector suitable for use in the microorganism of choice. The transformation vector is chosen so that the protein(s) will be over-expressed in the microbial cell biomass. This biomass is then used as a feed additive in such a way as to provide the viral or bacterial or fungal protein(s) directly to the animal, thus stimulating an immunological response to that particular pathogen. The microbial component may enter the body of the animal in the digestive tract, or otherwise through contact in the air or water.

Example 5

Vaccination Using Probiotic Feeds

Probiotic bacteria such as *Lactobacillus, Bacillus, Bifidobacterium*, etc. provide beneficial effects by their presence as live organisms in the digestive tract of an animal. As such, they are constantly replicating; they become a significant portion of the intestinal microflora and make an excellent continuous delivery mechanism for oral vaccines. Oral vaccines deliver the antigen to a portion of the intestinal mucosa where it can interact with immunogenic tissues (e.g., Peyers Patches) and stimulate an immunogenic response.

An antigen characteristic to a particular pathogen is chosen as is indicated by the animal and circumstances. For example, a viral coat protein or component thereof, or an infectious bacterial protein, or a component thereof is chosen. The gene coding for the protein is isolated and incorporated into a vector suitable for use in the probiotic microorganism of choice. Other gut microfloral components not generally considered as probiotics, but which live in the intestine, such as coliforms (e.g. *Escherichia coli*) can also be used as a vector for producing the vaccine in situ.

The two viral coat proteins from salmon infectious pancreatic necrosis virus (IPNV) are isolated and inserted into a transformation vector selected for use in *Lactobacillus* using molecular biology methods that are well known by those of skill in the art. The recombinant *Lactobacillus* cells expressing the viral antigens as free proteins, excreted proteins, and/or virus like particles (assembled viruses with no nucleic acid) are then grown using conventional fermentation technology, harvested, and processed into a form usable as a salmon feed. This form may include, but is not limited to, freeze drying, spray drying, fluid bed drying, microencapsulation, extrusion, or tableting. The recombinant *Lactobacillus* is then provided to the salmon as a feed, thereby delivering both the valuable probiotic as well as the vaccine. In this case, the vaccine is constantly produced as long as the recombinant *Lactobacillus* is present in the gut of the animal.

Example 6

Delivery of Active Peptides or Proteins Using Probiotic Feeds

The gene for an active antimicrobial peptide, such as, but not limited to, cecropins, peneaidins, bactenecins, callinectins, myticins, tachyplesins, clavanins, misgurins, pleurocidins, or parasins, or an antimicrobial protein (such as histones, acidic proteins, or lysozymes) is isolated and inserted into a transformation vector selected for use in *Lactobacillus* using molecular biology methods that are well known by those of skill in the art. The recombinant *Lactobacillus* cells, expressing the free peptides or proteins or excreted proteins, are then grown using conventional fermentation technology, harvested, and processed into a form usable as a feed for an animal such as, but not limited to, fish, crustaceans, livestock, etc. This form may include, but is not limited to, freeze drying, spray drying, fluid bed drying, microencapsulation, extrusion, or tableting. The recombinant *Lactobacillus* is then provided to the animal as a feed, thereby delivering both the valuable probiotic as well as the antimicrobial compound. In this case, the antimicrobial compound is constantly produced as long as the recombinant *Lactobacillus* is present in the gut of the animal.

Example 7

Cloning and Expression of Structural Protein Genes of Infectious Pancreatic Necrosis Virus (IPNV) in Yeast The West Buxton (WB) strain of IPNV (ATCC VR877) was purified as previously described (Yao and Vakharia 1998). The virus was propagated in Chinook salmon embryo cell culture (CHSE-214; ATCC CRL-1681) at 15° C. in Eagle's minimum essential medium (EMEM) and supplemented with 10% fetal bovine serum (FBS), 100 U/mL penicillin, 100 µg/mL streptomycin, and 1 µg/mL fungizone. Total viral RNA was isolated from the purified virus by digestion with proteinase K (200 mg/mL) followed by a standard phenol:chloroform extraction (Sambrook et al. 1989).

Complementary DNA (cDNA) of a segment of IPNV encoding a polyprotein comprising the IPNV structural proteins was obtained by reverse-transcription polymerase chain reaction (RT-PCR), cloned into pCR2.1 and pUC18, and completely sequenced. Clones with 100% identity to the published sequences for the VP2-NS-VP3 polyprotein were selected. These were removed from the cloning vector as an EcoRI fragment and ligated into a pESC-URA yeast expression vector (Stratagene, LaJolla, Calif.) which was linearized with EcoRI and dephosphorylated with calf intestine alkaline phosphatase by standard methods (Sambrook et al. 1989).

This expression vector was then used to transform XL1-B competent cells (Stratagene, LaJolla, Calif.) and colony selection was performed on Luria-Bertani agar with 12.5 µg/mL tetracycline and 50 µg/mL ampicillin. Using blue color selection in the presence of X-gal and IPTG, only white colonies were selected. Plasmid preparations were made from selected colonies using the Qiagen QIAprep spin column method (Qiagen, Valencia, Calif.) as described by the manufacturer. Restriction digestion with EcoRI verified the plasmids were 6.6 kb, as expected of pESC-URA.

Competent *Saccharomyces cerevisiae* YPH501 (Stratagene, LaJolla, Calif.) cells were made as described by the manufacturer. An overnight culture of YPH501 was diluted 1:20 in 50 mL of YPAD broth (1% yeast extract, 2% peptone, 0.0075% L-adenine hemisulfate, 2% dextrose) and grown at 30° C. to A600 equal to 1.0. Cells were then pelleted at 1000 g for 5 minutes at 4° C. The supernatant was discarded and the cells resuspended in LTE buffer (0.1 M lithium acetate, 10 mM Tris-HCl (pH 7.5), 1 mM EDTA). The resuspended cells were then centrifuged at 1000 g for 5 minutes at 4° C. The supernatant was discarded and pelleted cells resuspended in 0.5 mL of LTE buffer, and stored at 4° C. for one day before use.

Transformation of 50 µL of the YPH501 competent cells was performed in sterile 1.5 mL microfuge tubes by addition of 3 µg of purified IPNV/pESC-URA clone. The tube contents were mixed by inversion and incubated for 30 min at 30° C., and then heated to 42° C. for 15 minutes in a water bath. The tube contents were plated at 100 and 200 µL per plate on Synthetic Dextrose Minimal Medium (SD dropout medium). SD dropout medium is auxotrophic, and composed of 6.7 g of yeast nitrogen base without amino acids, 20 g dextrose, 1.3 g amino acid powder (13 amino acids plus adenine sulfate, no added uracil), 20 g agar per liter of medium. Plates were then incubated at 30° C. for 3 days, i.e., when colony formation was evident. These colonies appeared as viable colonies on a background of yeast that was dead or not growing in the auxotrophic medium, indicating they were capable of making their own uracil. These putative transformants were patch plated onto SD dropout plates and incubated again at 30° C. for 3 days. All of the clones selected were able to grow on the auxotrophic medium. The structural genes VP2 and VP3 have been reported to be expressed in a similar construct in insect larvae (Vakharia, 2003), and to form virus-like particles.

Two transformed clones were then inoculated into SG dropout medium (SD dropout medium with the dextrose replaced by an equal amount of galactose) to induce the GAL10 promoter, which controls the expression of the cloned foreign genes. Cells were grown at 30° C. with shaking for several days, then samples of the culture were periodically harvested and pelleted by centrifugation at 1500 g for 5 min at 4° C. Pelleted cells were broken by standard glass bead disruption techniques (Ausubel et al. 1997). The cells were resuspended in glass bead disruption buffer (20 mM Tris-HCl (pH 7.9), 10 mM $MgCl_2$, 1 mM EDTA, 5% glycerol (w/v), 1 mM DTT, 0.3 M ammonium sulfate, 1 mM PMSF, 5 mM benzamidine) and transferred to a 2 mL sterile Beadbeater tube (Biospec Products, Bartelville, Okla.) that was pre-filled to ½ volume with 0.5 mm acid-cleaned glass beads (Biospec Products). Cells were then placed on ice for at least 15 minutes. Cells were broken by pulsed-bead beating with 8 total pulses of 30 seconds with >1 minute intervals where the tubes were kept on ice. The Beadbeater tubes were centrifuged in a microfuge for 5 minutes at maximum microfuge speed (14,000 rpm). Supernatants were transferred to clean 1.5 mL microfuge tubes; 50 µL was removed to a clean 10×100 mm glass tube for determination of the concentration of total protein (Lowry et al., 1951) and the remainder stored at −20° C. until further processing.

Results of the Lowry assay were used to determine the volume of supernatant required to place 22 µg protein/lane into each of two pre-cast 12% polyacrylamide gels (BioRad, Hercules, Calif.) for sodium dodecyl sulfate-electrophoresis (SDS-PAGE). The two gels were run at 150 V (constant voltage) in the Micro Protean 3 system to separate the component proteins of the supernatants according to their molecular weight. One gel was stained with Coomassie Blue to detect the component proteins, and the proteins in the other gel were transferred directly to a nitrocellulose membrane by western transfer using the Micro Protean 3 cell (Bio-Rad, Hercules, Calif.) as directed by the manufacturer.

Western blotting followed standard procedures (Ausubel et al. 1997). Gels were equilibrated for 10-15 min in transfer buffer (25 mM Tris, 190 mM glycine, 20% methanol) and assembled as described by the Micro Protean 3 manufacturer. The gels were transferred to the nitrocellulose membrane at 300 mA (constant current) for 2 hours, while chilled with ice. The membrane was placed in TTBS buffer (20 mM Tris-HCl (pH 7.5), 0.1% Tween-20, 10 mM sodium chloride) and washed twice for 5 min. The membrane was then blocked in blocking buffer (TTBS with 1% casein, 2% BSA) for one hour with shaking, then washed twice with TTBS.

The membrane was incubated at room temperature for 1 h with shaking with a sheep polyclonal antibody to IPNV (Microtek, Sannichton, British Columbia, Canada) at a 1:1000 dilution in TTBS with 0.05% BSA. Following this incubation in primary antibody, the membrane was washed twice with TTBS then incubated with a secondary antibody, horseradish peroxidase-conjugated, affinity purified rabbit anti-sheep IgG (H+L) (Jackson Immuno Research, West Grove, Pa.), diluted 1:500 in TTBS with 0.5% BSA and normal rabbit serum (Bioresource International, Camarillo, Calif.). The secondary mixture was incubated for a minimum of 1 h at room temperature while shaking. The membrane was washed twice with TTBS then 1 Step TMB Blotting was performed according to the manufacturer's instructions (Pierce Chemical, Rockford, Ill.). Upon sufficient color development, the reaction was stopped by rinsing the membrane with water.

As seen in FIG. 1, multiple proteins are visible on the membrane as horizontal bands, distributed according to their molecular weight. The use of pre-stained molecular weight (MW) markers (Bio-Rad low MW) in lanes 1, 2, and 15 monitored the molecular weight distribution profile of the protein on the nitrocellolose post-transfer. The six major bands in these lanes are 103, 77, 50, 34.3, 28.8, and 20.7 kDa, respectively, from top to bottom. Lanes 3 and 4 of the membrane contain the proteins of the IPNV virus West Buxton strain, and the bands visible in FIG. 1 demonstrate viral proteins that are immunoreactive with the IPNV antibody.

Yeast clones A0244 and A0245 express the same three major immunoreactive proteins of approximately 60, 32, and 29 kDa. Each of the three proteins comigrated in the gel with an immunoreactive protein in the virus. The 60 kDa protein corresponds to VP2 and the 32 kDa protein corresponds to VP3.

As shown by the consistancy of the intensity of the immunoreactive bands in lanes 5-14, expression of the recombinant protein is maintained at a relatively constant level from the time the culture is started through the lag phase of growth, which indicates that harvesting clones for maximal biomass will provide optimal levels of recombinant protein.

Example 8

Incorporation of IPNV Gene-Containing Clones A0244 and A0245 into Fish Feed

The yeast mutants of Example 7 were grown in SG dropout medium at 30° C. with shaking for 5 days. Yeast were harvested by centrifugation at 2300 rpm in a Jouvan B3.11 centrifuge for 15 minutes at room temperature. A gel-forming medium was produced by mixing 1.5% waxy maize digestible starch (Ulra-Sperce M, National Starch and Chemical Co.), 1.2% sodium alginic acid (Sigma Chemical), and 4% Aqua Savor (Bentoli), the volume adjusted to 120 mL of $ddH_2O$, and the mixture warmed to dissolve the alginate (to about 40° C.). A stock solution of 5% $CaCl_2$ (Sigma) and 1% NaCl (Sigma) was prepared with tap water in a beaker, filled approximately half full. The harvested yeast cells were cracked with glass beads using 4 mm glass beads (Biospec Products) and 4×30 second pulses. The cracked cells were put into the gel-forming mixture at concentrations of 1% and 10%. The 1% yeast mixture was supplemented with an additional 9% (weight/volume) yeast (Fleischmann's Dry Powdered Rapid Yeast). A control feed containing 10% non-recombinant yeast was also produced.

Feeds with control, 1% mutant, and 10% mutant yeast were produced by squirting the yeast mixture from 100 mL syringes into the $CaCl_2$/NaCl solution, which was gently mixing, such that upon contact, solid materials were formed, which were quickly mixed together into strands of gelled feed. The gelled strands were strained through a screen with course gratings (1 mm) to provide materials of the correct size for feeding small fish. The feed was then washed with tap water on a fine screen, and stored at 4° C. until fed to fish.

Hybrid striped bass (from 1-1.5 g each) were fed 1 g of one of either control, 1% mutant, or 10% mutant yeast at a rate of 0.5 g of food per day for a week, followed by a week of normal diet, followed by an additional week of test diet as a booster. Fish were housed in a recirculating system with 20 L tanks filled with Instant Ocean-based artificial seawater. Plasma was collected from five fish at the beginning of the study as controls. An additional five fish from each treatment were sampled at the end of the second study week (one week after stopping the initial exposure to the yeast). The remaining fish were sampled at the end of the fourth week of the study, one week after the booster feeding. Blood was collected by caudal severing following MS222 anesthesia; the caudal fin was removed with scissors, blood collected from the tail with a capillary tube, and centrifuged to isolate the plasma, which was stored until analysis.

Example 9

Cloning and Expression of White Spot Virus Genes in Bacteria

Five genes from shrimp White Spot Virus (WSV) were cloned from the DNA of WSV recovered from the hemolymph of WSV-infected shrimp using RT-PCR to amplify the genes and the TOPO TA cloning system from Invitrogen. Clones with VP35, VP28, VP26, VP24, and VP19 genes were compared to the published WSV gene sequences (van Hulten et al., 2001), and clones with 100% identity selected for subcloning. The EcoRI fragments from the TOPO vector were sub-cloned into the pET28 vector from Novae (Madison, Wis.), previously cut with EcoRI and dephosphorylated. Clones containing EcoRI fragments were identified by color selection with IPTG and XGAL using standard methods (Sambrook et al. 1989). Protein expression was determined by growing the clones in LB medium and inducing protein expression with IPTG. The pET28 vector tags expressed proteins with a 6His tag, which was used to detect expression of the protein products of the WSV genes.

Figure 2:
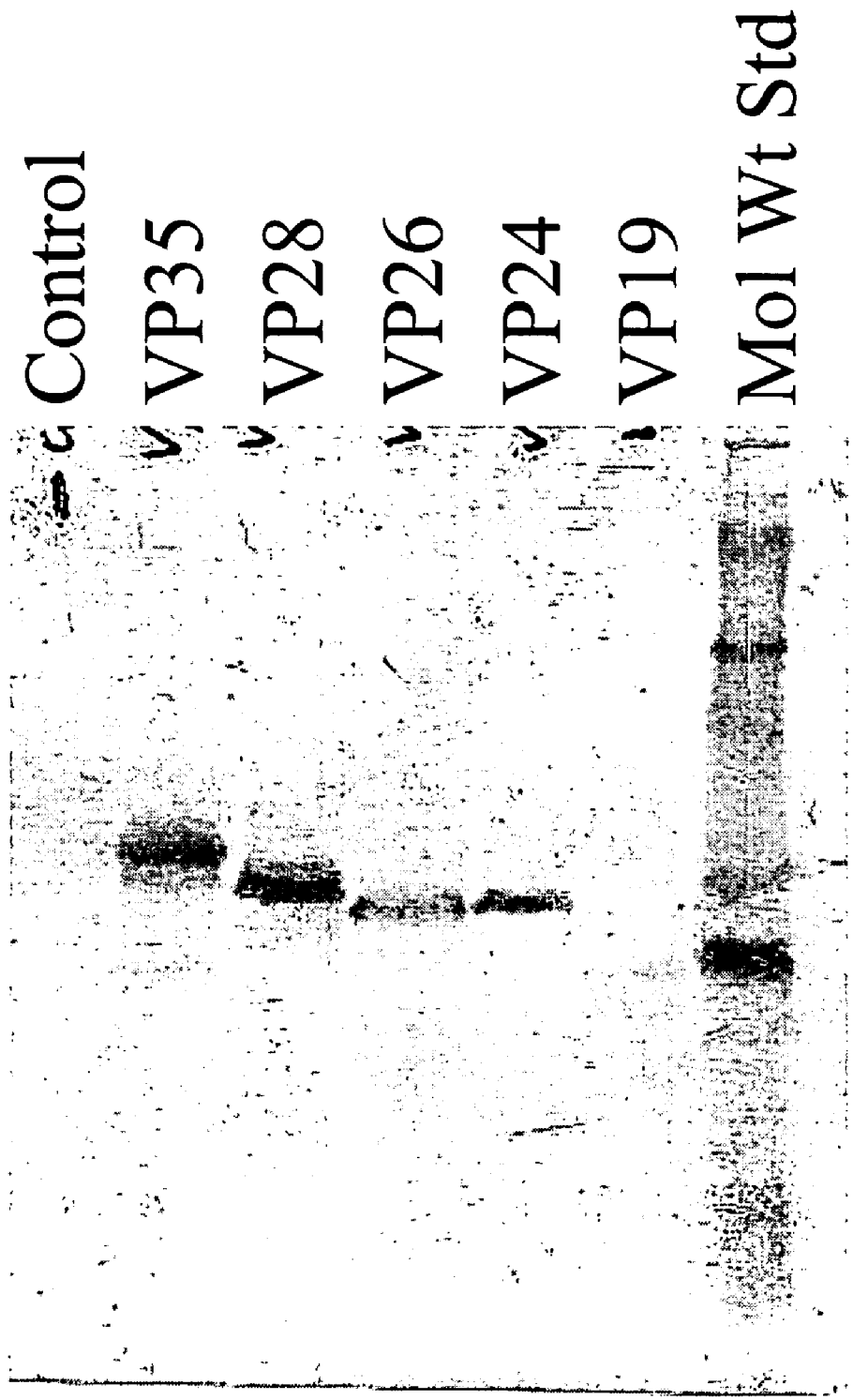

Expression was detected by SDS-PAGE followed by western blotting on Immobile-P membrane (Millipore) using standard methods (Sambrook et al. 1989). Anti-His antibody labeled with alkalin phosphatase coupled with NBI/BCIP color development was used to detect expression of VP35, VP28, VP26, VP24, and VP19. As shown in FIG. 2, all five clones produced His-tagged fusion proteins, which correspond to VP35, VP28, VP26, VP24, and VP19, respectively.

References

Ausubel F. et al. (1997) Short Protocols in Molecular Biology, 3rd ed. John Wiley & Sons, Inc., New York.
Lowry O, Rosebrough N, Farr A, Randall R (1951) Protein measurement with the Folin phenol reagent. J. Biol. Chem. 193:265-275.
Sambrook. J, Fritsch E, Maniatis T (1989) Molecular Cloning: A laboratory manual, 2 ed. Cold Spring Harbor Press, Cold Spring Harbor.
Vakharia V (2003) Sub-unit vaccine for infectious pancreatic necrosis virus. In: US Patent Publ 2003/0072772 A1. UMBI, USA.
van Hulten M C et al. (2001) The white spot syndrome virus DNA genome sequence. Virology 286:7-22.
Yao K, Vakharia V N (1998) Generation of infectious pancreatic necrosis virus from cloned cDNA. J Virol 72:8913-8920.

The invention claimed is:

1. A method of treating shrimp, wherein the method comprises feeding to the shrimp a fermented and homogenized fungal biomass containing at least one bioactive acidic bactericidal or bacteriostatic peptide expressed by the fungi during fermentation and cultured fungal cells, wherein the bioactive peptide is non-native to the fungi, and wherein the fermented and homogenized fungal biomass is fed to the shrimp in an amount sufficient to produce a bactericidal or bacteriostatic effect in the shrimp.

2. The method of claim 1, wherein the fermented and homogenized fungal biomass further comprises a protein from an infectious bacterium, which stimulates an immunologic response.

3. The method of claim 1, wherein the fermented and homogenized fungal biomass comprises yeast.

4. The method of claim 1, wherein the fermented and homogenized fungal biomass comprises *Mortierella*.

* * * * *